US006685915B2

(12) United States Patent
Uzgiris et al.

(10) Patent No.: US 6,685,915 B2
(45) Date of Patent: Feb. 3, 2004

(54) EXTENDED-LINEAR POLYMERIC CONTRAST AGENTS, AND SYNTHESIZING METHODS, FOR MEDICAL IMAGING

(75) Inventors: Egidijus Edward Uzgiris, Schenectady, NY (US); Terence Barnhart, Morristown, NJ (US)

(73) Assignee: General Electric Company, Niskayuna, NY (US)

( * ) Notice: Subject to any disclaimer, the term of this patent is extended or adjusted under 35 U.S.C. 154(b) by 73 days.

(21) Appl. No.: 09/803,794

(22) Filed: Mar. 12, 2001

(65) Prior Publication Data

US 2001/0028876 A1 Oct. 11, 2001

Related U.S. Application Data

(63) Continuation-in-part of application No. 09/451,719, filed on Dec. 1, 1999, now Pat. No. 6,235,264.

(51) Int. Cl.$^7$ .................. A61B 5/055; A01N 37/18; A61K 38/00; C07K 1/00; C07K 14/00; C07K 17/00
(52) U.S. Cl. .................. 424/9.34; 424/9.3; 424/9.36; 514/2; 514/12; 530/350
(58) Field of Search .................. 530/350; 424/9.3, 424/9.34, 9.36; 514/2, 12

(56) References Cited

U.S. PATENT DOCUMENTS

| | | | | |
|---|---|---|---|---|
| 5,230,883 A | * | 7/1993 | Kornguth et al. | 424/9 |
| 5,554,748 A | * | 9/1996 | Sieving et al. | 540/465 |
| 5,762,909 A | | 6/1998 | Uzgiris | 424/9.34 |
| 5,919,432 A | * | 7/1999 | Meyer et al. | 424/9.365 |
| 5,958,372 A | * | 9/1999 | Ladd | 424/1.65 |
| 6,235,264 B1 | | 5/2001 | Uzgiris | 424/9.36 |
| 6,274,713 B1 | * | 8/2001 | Sieving et al. | 530/402 |
| 6,372,194 B1 | * | 4/2002 | Akaike et al. | 424/9.323 |
| 2001/0028877 A1 | * | 10/2001 | Uzgiris | 424/9.364 |

OTHER PUBLICATIONS

Theodore, J. Passe, M.D. et al., *Tumor Angiogenesis: Tutorial On Implications For Imaging*, RSNA, 1997; 203: 593–600.
R. Abramovitch, et al., *Noevascularization Induced Growth of Implanted c6 Glioma Multicellular Spheroids: Magnetic Resonance Microimaging*. Cancer Research 55, 1956–1962, May 1, 1995.
C. Frouge et al., *Correlation Between Contrast Enhancement In Dynamic Magnetic Resonance Imaging Of The Breast And TumorSr Angiogenesis*, Invenstigative Radiology, Vol 29, No. 12, 1994, 1043–1049.
R. Brasch, M.D. et al., *Assessing Tumor Angiogenesis Using Macromolecular MR Imaging Contrast Media*, JMRI Jan./Feb. 1997; 7:68–74.

F. Demsar et al., *A MRI Spatial Mapping Technique For Microvascular Permeability aAnd Tissue Blood Volume Based On Macromolecular Contrast Agent Distribution*, MRM 37:236–2242 (1997).
E.E. Uzgiris, *Tumor Uptake Of Contrast Agents: The Role Of Molecular Conformation*, SMRM PRoceedings 1656 (1998).
H.F. Dvorak et al., *Vascular Permeability Factor/Vascular Endothelial Groth Factor, Microvascular Hyperpermeability, and Angiogenesis*, AJP May 1995, vol. 146, No. 5.
F. Scopinaro et al., *Technetium–99m Sestamibi: An Indicator of Breast Cancer Invasiveness*, Eur. J. Nuci Med (1994) 21:984–987.
L.D. Buadu, *Breast Lesions: Correlation of Contrast Medium Enhancement Patterns on MR Images With Histopathologic Findings and Tumor Angiogenesis*, Radiology, vol. 200, No. 3, pp. 639–649, Sep. 19, 1996.
N. Weidner, M.D. et al., *Tumor Angiogenesis and Metastasis–Correlation In Invasive Breast Carcinoma*, The New England Journal of Medicine, vol. 3224: 1–8, 1991.
E.F. Haran et al., *Tamoxifen Enhances Cell Death In Implanted MCF7 Breast Cancer By Inhibiting Endothelium Growth*, Cencer Research 54, 5511–5514, Nov. 1, 1994.
R.H. Austin et al., Stretch Genes, Physics Today, pp. 32–37, 1997.
PF Sieving et al., *Preparation and Characterization of Paramagnetic Polychelates and Their Protein Conjugates*, Bioconjugate Chem. 1:65–71, 1990.
D.A. Sipkins et al., *Detection Of Tumor Angiogenesis In Vivo by AvB3–Targeted Magnetic Resonance Imaging*, Nature Medicine, vol. 4, No. 5: 623–626, May 1998.
Pierre–Giles de Gennes, "Entangled Polymers", Physics Today, 06/83, pp. 33–39.
Pierre–Giles de Gennes, "Reptation of a Polymer Chain In The Presence of Fixed Obstacles", J. Chem. Physics 55, Jan. 18, 1971, pp. 572–579.
Paul F. Sieving, Alan D. Watson, and Scott M. Rocklage, "Preparation andCharacterization of Paramagnetic Polychelates and Their Protein Conjugates", Bioconjugate Chem. Vol 1, Jul. 31, 1989, pp. 65–71.

* cited by examiner

*Primary Examiner*—Sreeni Padmanabhan
*Assistant Examiner*—Lauren Q. Wells
(74) *Attorney, Agent, or Firm*—Toan P. Vo; Patrick K. Patnode

(57) ABSTRACT

Linear extended polymeric paramagnetic chelates for use as MRI contrast agents are synthesized by conjugating DTPA chelator moieties to higher than 90% of the monomer residues of the polyamino acid backbone chain. The resulting polymer can be labeled with Gd, since each chelator moiety holds a Gd ion, and the resulting conformation is of an unfolded, extended linear type, capable of entering small pores and moving around obstacles in the extracellular space of tissues. The efficient production of these extended polymers is critical for the application of such contrast agents to medical imaging. One such agent is a reptating polymer containing technetium-99.

9 Claims, 3 Drawing Sheets

EXTENDED-LINEAR POLYMERIC CONTRAST AGENTS, AND SYNTHESIZING METHODS, FOR MEDICAL IMAGING

CROSS REFERENCE TO RELATED APPLICATIONS

This application is a continuation-in-part of application Ser. No. 09/451,719, now U.S. Pat. No. 6,235,264 filed Dec. 1, 1999, the entire disclosure of which is hereby incorporated by reference.

BACKGROUND OF THE INVENTION

This invention relates to nuclear magnetic resonance imaging (MRI) and, more particularly, to extended-linear polymeric contrast agents for magnetic resonance imaging of tumors and methods of synthesizing such agents.

Tumor angiogenesis is the recruitment of new blood vessels by a growing tumor from existing neighboring vessels. This recruitment of new microvasculature is a central process in tumor growth and in the potential for aggressive spreading of the tumor through metastasis. All solid tumors require angiogenesis for growth and metastasis. Thus, the level of angiogenesis is thought to be an important parameter for the staging of tumors. Furthermore, new therapies are being developed which attack the process of angiogenesis for the purpose of attempting to control tumor growth and tumor spread by restricting or eliminating the tumor blood supply. It is therefore of clinical importance to be able to monitor angiogenesis in tumors in a noninvasive manner.

To assess angiogenic activity of tumors, two parameters are of primary importance: vascular volume and vascular permeability. Invasive techniques utilizing tissue staining can be used to assess microvascular development, but the sensitivity of existing staining methods is not high enough and the prognostic value of such methods is not yet well established (N. Weidner, et al., *New Eng. J. Med.* 324:1–8, 1991). At present there is no single imaging method capable of providing quantitative characterization of tumor angiogenesis.

As for non-invasive methods for assessing the two parameters, the parent application Ser. No. 09/451,719 "now U.S. Pat. No. 6,235,264", teaches a magnetic resonance imaging method with a type of contrast agent that enables measurement of both vascular volume and vascular permeability with much higher sensitivity than heretofore possible. Such measurement should facilitate independent prognostic assessments of cancer and help in monitoring cancer therapy non-invasively.

When a substance such as living tissue is subjected to a uniform magnetic field (polarizing field $B_0$), individual magnetic moments of the nuclear spins in the tissue attempt to align with this polarizing field along the z axis of a Cartesian coordinate system, but process about the z axis direction in random order at their characteristic Larmor frequency. If the substance, or tissue, is subjected to a magnetic field (excitation field $B_1$) which is in the x-y plane and at a frequency near the Larmor frequency, the net aligned longitudinal magnetization may be rotated, or "tipped", into the x-y plane to produce a net transverse magnetization. A signal is emitted by the excited spins after the excitation signal $B_1$ is terminated. This NMR signal may be received and processed to form an image.

When utilizing NMR signals of this type to produce images, magnetic field gradients ($G_x$ $G_y$ and $G_z$) are employed. Typically, the region to be imaged is scanned with a series of measurement cycles in which these gradients vary according to the particular localization method being used. The resulting set of received NMR signals is digitized and processed to reconstruct the image using one of many well known reconstruction techniques.

One of the mechanisms employed in MRI to provide contrast in reconstructed images is the $T_1$ relaxation time of the spins. After excitation, a period of time is required for the longitudinal magnetization to fully recover. This period, referred to as the $T_1$ relaxation time, varies in length depending on the particular spin species being imaged. Spin magnetizations with shorter $T_1$ relaxation times appear brighter in MR images acquired using fast, $T_1$ weighted NMR measurement cycles. A number of contrast agents which reduce the $T_1$ relaxation time of neighboring water protons are used as in vivo markers in MR images. The level of signal brightness, i.e., signal enhancement, in $T_1$ weighted images is proportional to the concentration of the agents in the tissue being observed.

In pre-clinical research applications, high-field MRI has been used to assess tumor volume and tumor signal changes in animal models after treatment with tamoxifen, a type of antiangiogenic agent (H. E. Maretzek, et al., *Cancer Res.*, 54:5511–5514, 1994). By using an intravascular contrast agent, albumin-Gd-DTPA, tumor vascular volume and permeability were measured as well as spatial distribution of the neovasculature. In another study using a high polarizing field, tumor growth was followed by using a variety of NMR measurement pulse sequences that allowed the investigators to distinguish microvessels from larger vessels through blood oxygen level dependent effects. Permeability was assessed by noting the time dependent changes in NMR signal when Gd-DTPA was administered to the animal (R. Abramovitch, et al., *Cancer Res.* 55:1956–1962, 1995).

At lower polarizing fields that are available at clinical sites, Gd-DTPA, an MRI contrast agent approved by the FDA (U.S. Food and Drug Administration) has been used to estimate angiogenic activity of tumors (C. Frouge, et al., *Invest. Radiol.* 29:1043–1049, 1994). However, this contrast agent is not ideal for characterizing tumor vasculature because it rapidly migrates to the extravascular space before being excreted through the kidneys. The tumor NMR signal measurements become delicate, being based on the dynamics of contrast agent uptake and elimination. Staging of tumors by this approach has been difficult (R. Brasch, et al., *Radiology* 200:639–649, 1996).

To avoid the delicate dynamic aspects of Gd-DTPA uptake measurements, others have used a macromolecular contrast agent, albumin—Gd-DTPA (F. Demser, et al., *Mag. Res. Med.* 37:236–242, 1997). In this instance, the elimination process does not play a role in the observed MR signals, so that a much simpler and more reliable signal analysis is possible. Thus, MR signals based on $T_1$ changes (proportional to agent concentration) have provided indications of tumor blood vessel leak rate and tumor blood volume. This then represents an effective imaging method for assessing tumor angiogenesis. A severe drawback to this approach, however, is that this macromolecular agent has associated immune reactions when injected and leads to substantial toxicities. Thus, at present, this contrast agent is unsuitable for clinical applications (T. J. Passe, et al., *Radiology* 230:593–600, 1997).

BRIEF SUMMARY OF THE INVENTION

In a preferred embodiment of the invention, a contrast agent for use in acquiring MRI images for the purpose of assessing tumor angiogenesis comprises a reptating polymer containing gadolinium. Methods for synthesizing this polymer and linear extended polymeric paramagnetic chelates for use as MRI contrast agents are provided wherein DTPA (diethylene triamine pentaacetic acid) chelator moieties are conjugated to higher than 90% of the monomer residues of the polyamino acid backbone chain. The resulting polymer can be labeled with Gd, since each chelator moiety will hold a Gd ion, and the resulting conformation is of an unfolded, extended linear type, capable of entering small pores and moving around obstacles in the extracellular space of living tissues. Efficient production of these extended polymers is critical for the application of such contrast agents to medical imaging.

DETAILED DESCRIPTION OF THE INVENTION

Figure 1:
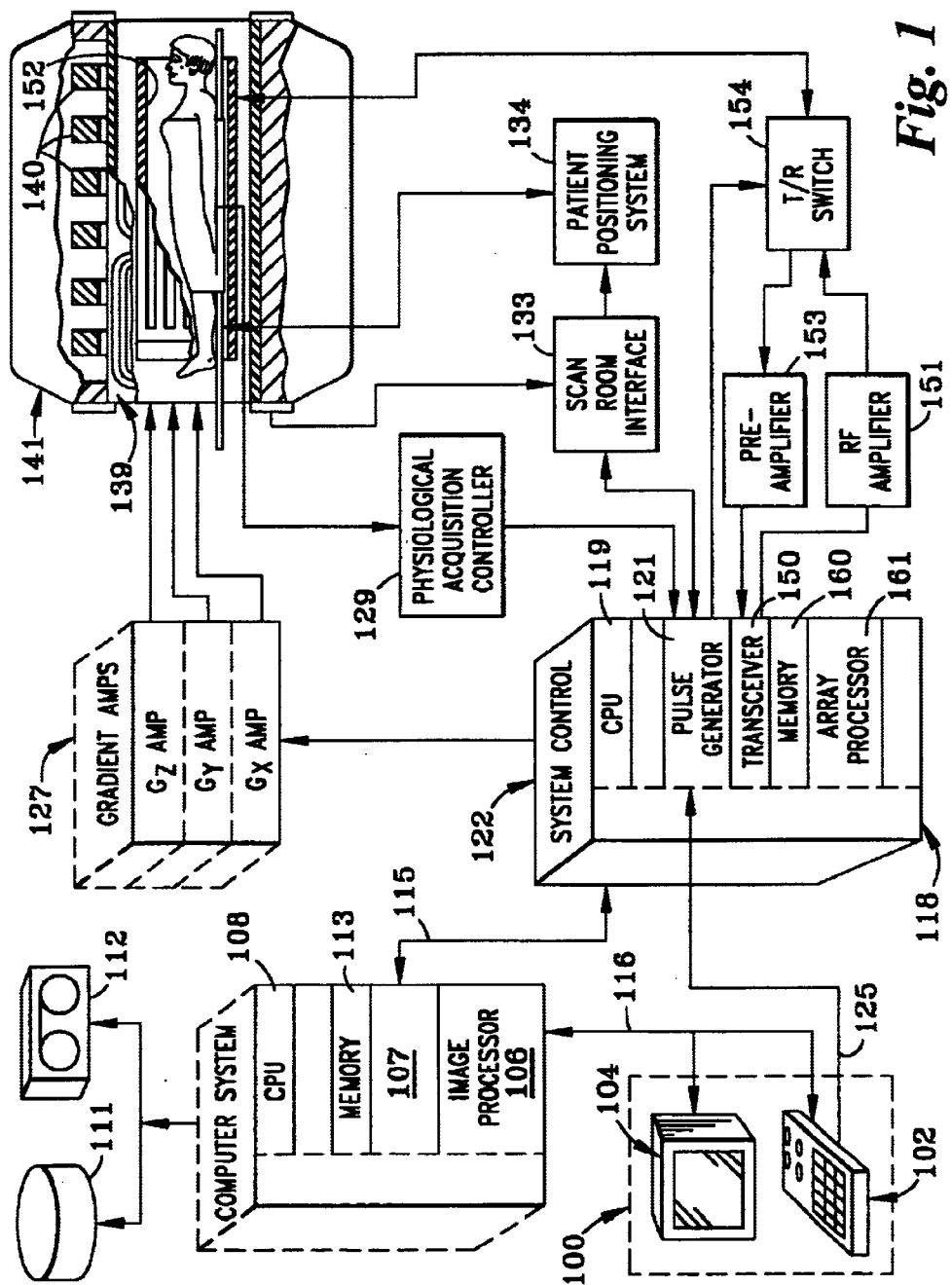
FIG. 1 is a block diagram of an MRI system which employs contrast agents of the present invention.

In characterizing tumor angiogenesis, a contrast agent comprising a reptating polymer is intravenously injected and a series of timed medical images is obtained. A signal enhancement (in $T_1$ weighted images) above a certain threshold, preferably 10%, constitutes an indicator of angiogenic activity. Signals beyond the threshold level will indicate increased angiogenic activity in the form of increased microvascular density, usually at the periphery edges of the tumor, and increased vascular permeability at the periphery and throughout the interior of the tumor.

One contrast agent for characterizing tumor angiogenesis is a reptating polymer, preferably as described in Uzgiris U.S. Pat. No. 5,762,909, issued Jun. 9, 1998 and assigned to the instant assignee. U.S. Pat. No. 5,762,909, incorporated by reference herein, describes the creation of elongated, worm-like macromolecules. A particularly preferred polymer is a homopolymer of lysine where the lysine residues are substituted with Gd-DTPA, or gadolinuim- diethylentriaminepentaaceticacid. The degree of substitution must be very high, in excess of 90%, for the polymer to assume an elongated worm-chain conformation. The polymers described in U.S. Pat. No. 5,762,909 have such a conformation as determined by their measured persistence length (in the range of 100 to 600 Å) which is similar to the persistence length of double-stranded DNA. Double-stranded DNA is a classic reptating polymer and is separated according to length in gel electrophoresis by the mechanism of reptation (R. H. Austin, et al., *Physics Today*, pp. 32–37, 1997). The polymers of U.S. Pat. No. 5,762,909 remain in the vasculature as a blood pool agent and leak out of the endothelium only in tumors which have a hyperpermeable endothelium. The hyperpermeability is a result of angiogenesis signals emanating from tumor cells under nutrient and oxygen stress. The polymers are shown to be ideal agents for MR imaging methods to measure tumor blood volume and tumor endothelium permeability. The polymers for use in characterizing tumor angiogenesis are made by substituting the lysine residues of polylysine with DTPA in a mixed anhydride reaction (Sieving, et al. *Bioconjugate Chem.* 1:65–71, 1990). However, in order to attain the reptating conformation, the anhydride reaction and the coupling reaction are modified: the synthesis of the anhydride of DTPA is as previously described by Sieving, but the reaction is preferably run between −25° C. and −28° C. for 30 minutes under dry nitrogen atmosphere. The coupling of the anhydride to the lysines is modified in that a much higher molar ratio of anhydride to lysines residues is used in the coupling (from 7 to 10). After the coupling reaction, the reaction solution is subject to roto-vaporation at 50° C. to release all the volatile organic molecules and then the product is purified through extensive dia-filtration (Amicon, 10 kD molecular weight cutoff filters). To achieve the final MR active agent, the paramagnetic ion gadolinium is incorporated into the product polymer chelating DTPA groups by dropwise addition of $GdCl_3$ in 0.1 M HCl (50 mM in Gd) into the polymer solution (15 mM $NaHCO_3$). The dropwise addition of Gd continues until a slight indication of free Gd (not chelated by available DTPA groups) is noted (small aliquots of polymer solution added to 10 $\mu$M of arzenzo III in acetate buffer-free Gd turns the dye solution blue). The reptating polymer is then introduced into a blood vessel of the subject.

Other paramagnetic ions besides Gd may be used. However, Gd is the most paramagnetic (i.e., has the most unpaired electrons) and thus is the most effective as contrast agent. A chelator such as DTPA must be used because free Gd is toxic. The chelator folds around the Gd and tightly binds it, but the water protons can come into one Gd coordination site and be relaxed.

A comparable Lanthanide series element that can be used is Dy, dysprosium. All other elements are less effective in relaxing water protons. Iron and manganese (MN(II) and Fe(III) have also been used with much less relaxivity per ion by a factor of about 3 for the DTPA chelate.

The uptake of these molecules, as judged by MR signal enhancements, is more than ten times higher than observed for other macromolecular agents such as compact coiled peptide agents or globular protein, albumin-Gd-DTPA, agents. The extravasation of the polymeric agents in the tumors is thought to be much higher than for the globular agents due to the process of reptation, which allows the polymers to migrate around obstacles in a small convective force field. The globular agents, on the other hand, cannot move through very small pores or around obstacles in a fibrous matrix of the basement membrane of the endothelium and are thus repelled and mostly remain in the blood circulation before being cleared out through the renal or hepatobiliary excretion channels. Hence, globular agents give small tumor signals and small signals of tumor permeability when injected intravenously.

If a relatively short chain length polymeric agent (typically about 150–250 monomers or residues) is used, the signal will be reduced from a longer chain of about 500 residues by perhaps a factor of 4 for well-known reasons having to do with circulation times and the physics of the reptation process. However, the signal response will be faster and the faster blood clearance will be a desirable feature for monitoring and following effects of antiangiogenesis therapy.

Reptating polymers as taught in the parent application Ser. No. 09/451,719 are synthesized either from a homopolymer such as polylysine or from random co-polymers of glutamic acid and lysine. The random co-polymers are more suitable for synthesis of short chain agents and allow for a more robust synthesis procedure.

Figure 2:
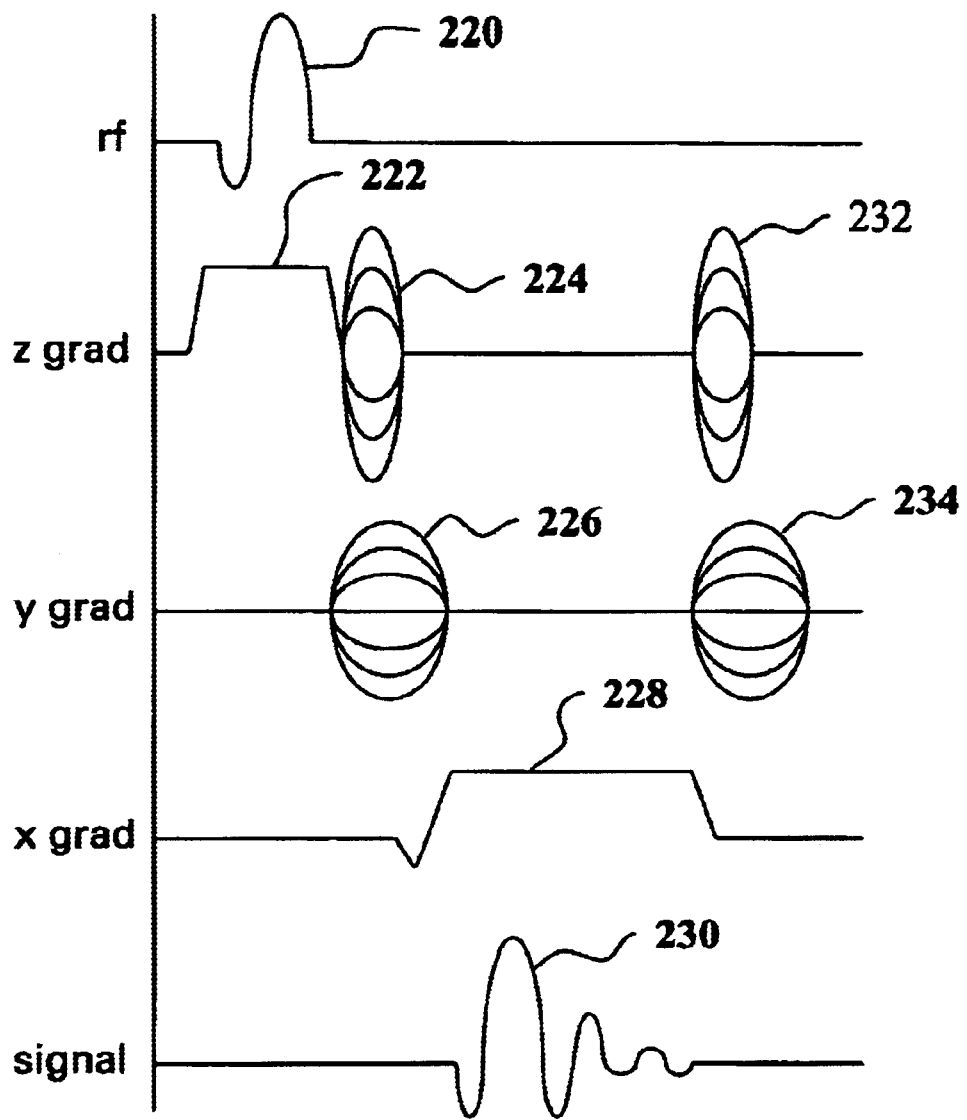
FIG. 2 is a graphic representation of a pulse sequence performed by the MRI system of FIG. 1 to assess tumor angiogenosis.

In order to assess tumor angiogenesis in accordance with an embodiment of the parent application Ser. No. 09/451,719, a subject is first imaged and then the contrast agent is introduced into the subject by injecting the contrast agent intravenously at approximately 0.025 moles Gd/Kg. The subject is then imaged again, preferably beginning immediately after injection and at certain timed intervals. Preferably, the timed intervals are shortly after injection (within 10 minutes) and up to 1 hour post injection. For highest sensitivity of permeability, an image at 24 hours may also be acquired. FIGS. 1 and 2, as described below, illustrate a preferred MRI imaging procedure. To determine changes in blood volume, imaging should take place within 10 minutes of contrast agent injection.

FIG. 1 shows the major components of a preferred MRI system which can be used in practicing the invention. Operation of the system is controlled from an operator console 100 which includes a keyboard and control panel 102 and a display 104. Console 100 communicates through a link 116 with a separate computer system 107 that enables an operator to control the production and display of images on the screen of display 104. Computer system 107 includes a number of modules which communicate with each other through a backplane 120. These include an image processor module 106, a central processing unit (CPU) module 108 and a memory module 113, known in the art as a frame buffer for storing image data arrays. Computer system 107 is linked to a disk storage 111 and a tape drive 112 for storage of image data and programs, and communicates with a separate system control 122 through a high speed serial link 115.

System control 122 includes a set of modules connected together by a backplane 118. These include a CPU module 119 and a pulse generator module 121 which is coupled to operator console 100 through a serial link 125. Through link 125, system control 122 receives commands from the operator which determine the scan sequence that is to be performed.

Pulse generator module 121 operates the system components to carry out the desired scan sequence, and produces data which determine the timing, strength and shape of the RF pulses to be produced, and the timing and length of the data acquisition window. Pulse generator module 121 is coupled to a set of gradient amplifiers 127, to determine the timing and shape of the gradient pulses to be produced during the scan. Pulse generator module 121 also receives patient data from a physiological acquisition controller 129 that receives signals from a number of different sensors attached to the patient, such as electrocardiogram (ECG) signals from electrodes or respiratory signals from a bellows. Pulse generator module 121 is also coupled to a scan room interface circuit 133 which receives signals from various sensors associated with the condition of the patient and the magnet system. Through scan room interface circuit 133, a patient positioning system 134 receives commands to move the patient to the desired position for the scan.

Gradient amplifier system 127 that receives gradient waveforms from pulse generator module 121 is comprised of $G_x$, $G_y$ and $G_z$ amplifiers. Each gradient amplifier excites a corresponding gradient coil in an assembly 139 to produce the magnetic field gradients used for position encoding acquired signals. Gradient coil assembly 139 forms part of a magnet assembly 141 which includes a polarizing magnet 140 and a whole-body RF coil 152. A transceiver module 150 in system control 122 produces pulses which are amplified by an RF amplifier 151 and coupled to RF coil 152 by a transmit/receive switch 154. The resulting signals radiated by the excited nuclei in the patient may be sensed by the same RF coil 152 and coupled through transmit/receive switch 154 to a preamplifier 153. The amplified NMR signals are demodulated, filtered, and digitized in the receiver section of the transceiver 150. Transmit/receive switch 154 is controlled by a signal from pulse generator module 121 to electrically connect RF amplifier 151 to coil 152 during the transmit mode and to connect preamplifier 153 to coil 152 during the receive mode. Transmit/receive switch 154 also enables a separate RF coil (for example, a head coil or surface coil) to be used in either the transmit or receive mode.

The NMR signals picked up by RF coil 152 are digitized by transceiver module 150 and transferred to a memory module 160 in system control 122. When the scan is completed and an entire array of data has been acquired in memory module 160, an array processor 161 operates to Fourier transform the data into an array of image data. These image data are conveyed through serial link 115 to computer system 107 where they are stored in disk storage 111. In response to commands received from operator console 100, these image data may be archived on tape drive 112, or may be further processed by image processor 106 and conveyed to operator console 100 for presentation on display 104.

Although the invention can be used with a number of different pulse sequences, a preferred embodiment of the invention employs a fast 3D (three dimensional) rf (radio frequency) phase spoiled gradient recalled echo pulse sequence, depicted in FIG. 2, to acquire the NMR image data. The pulse sequence "3dfgre" available on the General Electric 1.5 Tesla MR scanner sold by General Electric Company, Milwaukee, Wis., under the trademark "SIGNA" with revision level 5.5 system software is used.

As shown in FIG. 2, an RF excitation pulse 220 having a flip angle of from 40° to 60° is produced in the presence of a slab select gradient pulse 222 to produce transverse magnetization in the three-dimensional (3D) volume of interest as taught in Edelstein et al. U.S. Pat. No. 4,431,968, issued Feb. 14, 1984 and assigned to the instant assignee. This is followed by a slice encoding gradient pulse 224 directed along the z axis and a phase encoding gradient pulse 226 directed along the y axis. A readout gradient pulse 228 directed along the x axis follows, and a partial echo (60%) NMR signal 230 is acquired and digitized as described above. After the acquisition, rewinder gradient pulses 232 and 234 rephase the magnetization before the pulse sequence is repeated as taught in Glover et al. U.S. Pat. No. 4,665,365, issued May 12, 1987 and assigned to the instant assignee. As is well known in the art, the pulse sequence is repeated and the respective slice and phase encoding gradient pulses 224 and 226 are stepped through a series of values to sample the 3D k-space.

The acquired 3D k-space data set is Fourier transformed along all three axes and a magnitude image is produced in which the brightness of each image pixel indicates the NMR signal strength from each corresponding voxel in the 3D volume of interest.

An initial signal is then compared with the signal enhancement observed at selected times, preferably a short time after injection (within 10 minutes) and then at several time points up to 60 minutes post injection. For highest sensitivity to measure endothelial permeability of the tumor, a subsequent image at about 24 hours may also be taken. The initial image after injection (within 10 minutes) provides a measure of tumor blood volume or microvascular density, for each pixel of the image. Subsequent images then establish the rate of leakage into the tumor interstitium, again on a pixel by pixel basis. Maps of blood volume and of endothelium permeability may then be generated and displayed as an image or overlaid on the MR image directly. Both anatomical and physiological features will then be displayed simultaneously, giving radiologists not only the level of angiogenesis as an average quantity but also its activity as a function of position, a very desirable feature for staging and prognosis.

Signal enhancements at the endpoint of about 24 hours, that are below some threshold value, preferably about 10% (for the canonical dose of 0.025 mmoles Gd/Kg), signify minimal angiogenesis activity, as the examples given below imply. Higher signal values (preferably 75%, most preferably 90%) imply ever increasing angiogenic activity. The endpoint signals at 24 hours are due to capillary leakage, as blood concentration levels at that time will be negligibly small for the reptating polymer contrast agents described in the parent application Ser. No. 09/451,719 (although this would not be true for globular protein agents whose blood circulation time constant may be 24 hours and longer). In growing tumors, the endpoint signals may be expected to be as high as 200% in peripheral regions where neovasculature development is at its highest during angiogenesis.

The reptating polymer contrast agent confers a number of advantages over previous methods that involved the use of small extracellular agents or large macromolecular agents.

First, the polymeric agent does not leave the tumor at an appreciable rate over many hours, thus simplifying the uptake dynamics upon which the assay for angiogenesis is based.

Second, the signal changes observed with the reptating polymer agent are approximately 10 times higher than observed with an albumin agent or with the extracellular agent Gd-DTPA. Thus, this reptating polymer contrast agent provides a much higher sensitivity to changes in tumor permeability and yields significant changes in signal over the entire tumor volume unlike what is observed for the albumin agents.

Third, vascular permeability probed with a reptating polymer may be qualitatively different from that probed with a large globular protein such as albumin: the endothelial layer structures that result in the observed leakage in these two instances may be different. In the latter instance, a fragmentation of the basement membrane is required as well as existence of loose endothelial cell junctions for the albumin to be transported out of the vasculature. For reptating polymers, the junctions may be tighter, the basement membrane may not need to be as fragmented, or there may be specific transport mechanisms involving transendothelial transport. For example, in the tumor stroma, considerable levels of fibrinogen are found. This plasma protein has a long, extended conformation and high negative charge. The accumulation of fibrinogen in tumors appears to be associated with angiogenesis and is necessary for conversion of the extracellular matrix into a form conducive to cell growth. Thus, the uptake of the reptating polymer (which is also of high negative charge and is extended in form) may mimic the natural transport processes associated with angiogenesis much more closely than will the uptake of globular proteins.

Fourth, as observed by MRI signal changes, there appears to be little accumulation of the polymeric agent in organs such as liver, kidney or muscle. The clearance of the agent from these organs appears to follow the blood circulation decay rate and no trapping or prolonged binding is evident in these tissues. Furthermore, the blood circulation times can be adjusted by varying the polymer length. For short polymers (of 140–150 residues) the circulation time constant can be as short as 15 minutes (equal to the circulation time of the extracellular agent, Gd-DTPA). Thus, at present, there are no indications that toxicity will become an issue with these types of agents.

In addition to MRI, it is also possible to use nuclear imaging techniques with the polymeric agents. Presently the Gd is chelated in the DTPA polymer chain. It is possible to incorporate, for example, technetium-99 as well as the Gd in such a polymer. The agent uptake will still occur by the reptation mechanism. However, the imaging would be made in this instance through nuclear gamma radiation detection. This can be an alternative to the technetium-99 technique for angiogenesis evaluation with the advantages of a higher uptake of the reptating polymer agent.

It has been shown that linear extended polymeric contrast agents of suitable cross section are capable of enhancing the MRI contrast of tumors to a much larger extent than clinical extracellular agents or large globular agents such as labeled protein agents (U.S. Pat. No. 5,762,909; E. E. Usgiris, *ISRM Proc.* 1998, p. 1656). The synthesis of such agents has been described previously and relied on methods developed earlier by Sieving et al. (*Bioconjugate Chem.* 1:65–71, 1990). However, the synthesis procedure involving the anhydride method as delineated by Sieving does not provide the desired high conjugation efficiency necessary to achieve an elongated state.

The anhydride method involves conversion of the chelator molecule DTPA to an anhydride which then can react with an amine group of the lysines of a polylysine amino acid chain. The product polymer is thus a chain in which lysine groups are conjugated with DTPA. The usual degree of conjugation achieved was about 85%, and only rarely did the conjugation reach into the 90% range. Yet such high conjugation is necessary for the linear extended conformation to be achieved. The reaction was not well enough understood to predict what to change in the procedures to achieve a higher degree of conjugation. For example, a change in the anhydride to lysine molar ratio to higher values, a natural adjustment to favor higher lysine substitution, did not yield reliable improvements in the conjugation efficiency. The generation of the anhydride and the coupling reaction to polylysine, each follow complex kinetics and it was not obvious whether efficiency higher than 85% could be achieved consistently in this reaction scheme (particularly for longer chains which may have more propensity to physically sequester residual free lysine groups during the reaction).

A surrogate marker for conformation is the proton relaxivity of the polymer agent. If the agent is in a tightly coiled state, steric hindrance prevents free rotation of DTPA around the epsilon bond to the peptide backbone. If rotation is hindered, the relaxivity is increased owing to the longer rotational correlation time of the agent—relaxation of water protons becomes more effective (R. B. Lauffer, *Chem. Rev.* 87:901, 1987). Conversely, if the correlation time is shortened the water proton relaxation rate decreases. This can result if the rotation around the epsilon bonds of each DTPA is allowed, as would happen if the polymer backbone is fully extended and the invidividual DTPA moieties are not sterically restricted. This effect has been observed for example when the first few exposed lysine groups of the protein albumin are conjugated with DTPA (M. Spanoghe et al., *Magn. Reson. Imaging* 10:913, 1992).

Figure 3:
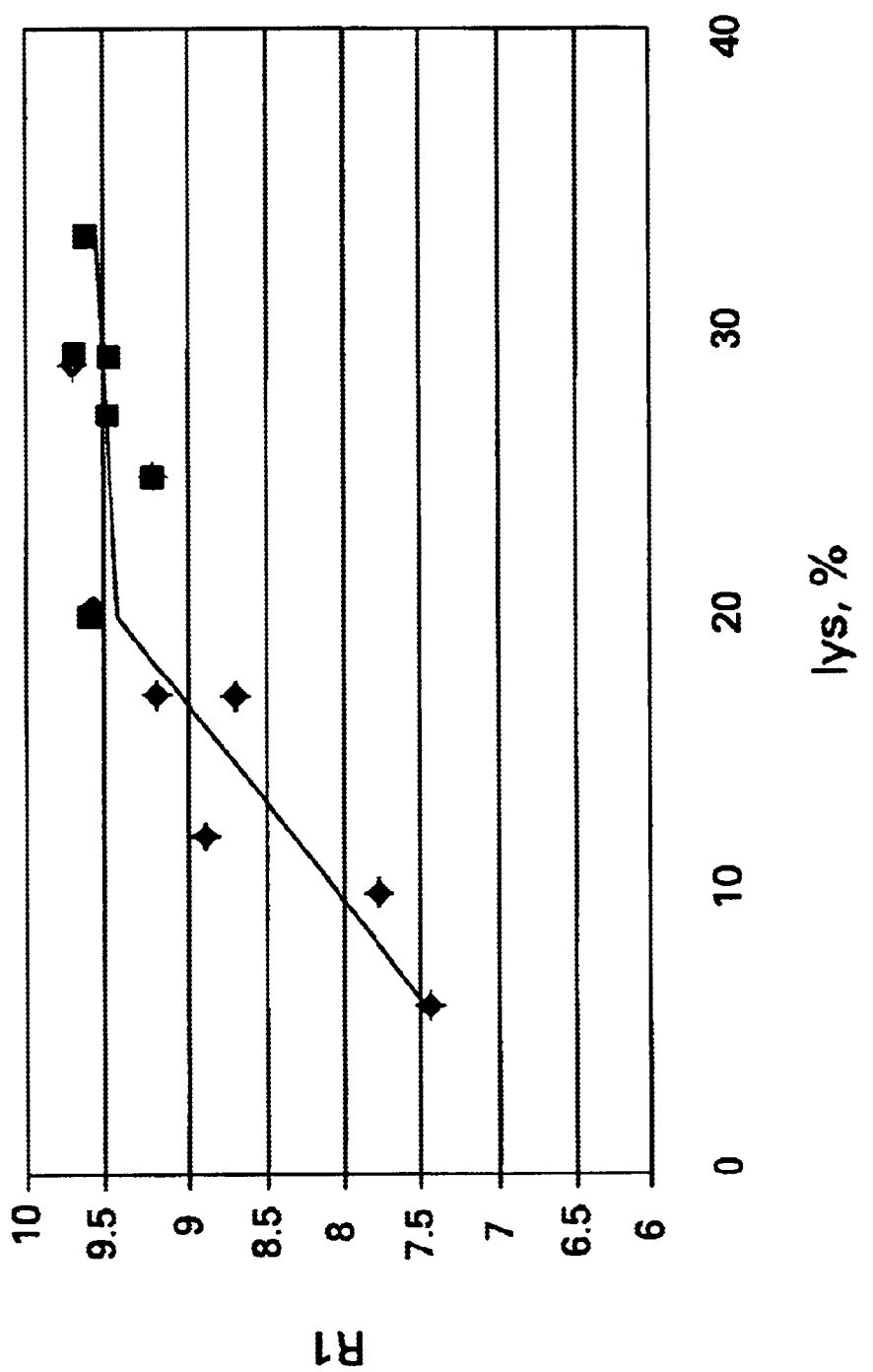
FIG. 3 is a graphic representation of the relationship between proton relaxivity and lysine content for linear extended polymeric paramagnetic chelates usable as MRI contrast agents.

FIG. 3 shows the relationship of proton relaxivity to free lysine content of the linear extended polymeric agents. As the lysine content is decreased below 20%, the polymer chain becomes less and less folded. The chain is fully extended, with relaxivity at a minimum plateau, for lysine content below about 7–10%. Likewise, as the lysine content increases beyond 20%, an upper plateau of about 10 to 11 relaxivity units is reached, indicating that the propensity to fold up into a coiled state is driven by the lysine content of the chain as it increases from below 10% to higher values. The folding conformation must be driven in part by ionic charge interactions between positive lysine groups and negatively charged DTPA groups, and will lead to tightest folding when there are nearly equal amounts of DTPA and lysine groups on the polymer chains. The folding is fairly complete by the time the lysine content in the polymeric chelate is 20% of monomer units.

Efficacy in imaging of tumor lesions arises from the ability of the agent to penetrate through the tumor endothelium, which is promoted dramatically if the polymer is in an extended state capable of reptation, i.e., ability to move around obstacles in snake-like fashion and the ability to penetrate through small diameter pores (P-G de Gennes, *Physics Today*, June 1983, p. 33). Coiled polymers present a large cross-section and cannot penetrate small pores in the endothelium, so that their effectiveness in marking tumors is much reduced. It is thus essential to produce let polymers of extended, uncoiled conformation, to be useful for medical imaging applications.

Because the kinetics of the anhydride reaction and the coupling reaction are evidently complex, simple manipulations of variables singly do not lead to improvements in conjugation efficiency. Evidently there is a coupling between some of the variables which confounds the interpretation of simple manipulations. The isolation of the key variables was demonstrated in a design of experiments, DOE, procedure in which each of 5 variables was manipulated simultaneously in between high and low levels, with center points chosen between high and low levels, (Box, G. E. P. et al., *Statistics for Experimenters*. 1978, John Wiley and Sons, New York).

Variables used in the study included reaction temperature, the TEA to DTPA ratio, the IBCF to DTPA ratio, the concentration of bicarbonate buffer, and the volume of bicarbonate buffer in which the polylysine was dissolved. The ranges for these variables are given in Table 1.

In general, to produce a purified DTPA substituted polymer in accordance with a preferred embodiment of the invention, a polylysine salt, such as poly-L-lysine hydrobromide, is dissolved in a 0.1 M aqueous sodium bicarbonate solution having a pH in the range of between about 8 and about 9.5, which is then cooled to about 0° C. Then DTPA and an acid acceptor are added to a dipolar aprotic solvent, preferably dry, nitrogen purged acetonitrile. This second solution is stirred until the DTPA is dissolved. Under a dry nitrogen purge, this second solution is cooled down to at least a temperature of −35° C. and an alkyl chloroformate, such as isobutylchloroformate, is added to this second solution to form a slurry. The slurry is then added to the cooled polylysine/sodium bicarbonate solution under vigorous mixing, and the resulting mixture is allowed to warm slowly to room temperature and is stirred for 15 to 20 hours. Standard biological separation techniques yield the purified DTPA substituted polymer, which may then be derivatized further with appropriate cationic species such as Fe, Gd, Tc or Mn.

In single variable testing, it was known that the DTPA anhydride/lysine molar ratio was important, and that ratios in excess of 6 yielded essentially similar results. Therefore, the ratio of DTPA anhydride to lysine residue ratio was set at or above 6 for the entire DOE, and not included as an independent variable. Temperature was also known to be a factor, but appeared non-linear, and was included in the DOE.

Several of the variables appear to affect the reaction. The primary effect of temperature overwhelms the DOE in its entirety, with high temperature (−15° C.) data points yielding completely unsatisfactory polymer. Relaxivity tests on these materials yield meaningless results. However, when the low temperature (−45° C.) quadrant is analyzed independently, other variables demonstrate increased importance. Merely using sufficient DTPA anhydride, and dropping the temperature of the anhydride reaction is insufficient to yield consistent, highly conjugated polylysine. Moving the remainder of the variables to the highest performing corner achieved consistent conjugation of between 93 and 97%.

TABLE 1

Variation of reaction variables in a DOE configuration.

| DTPA | TEA | Temp. IBCF | (IBCF) | [Bicarb] | Bicarb Volume | PL | Conjug % | RI |
|---|---|---|---|---|---|---|---|---|
| 1.2107 | 2.25 | 0.28 | −15 | 1 | 14 | 0.113 | ~45 | |
| 1.2137 | 2.24 | 0.44 | −45 | 0.1 | 6 | 0.12137 | 94 | 7.4 |
| 1.214 | 2.1 | 0.28 | −45 | 1 | 14 | 0.1214 | 80 | 9.5 |
| 1.2121 | 2.15 | 0.36 | −30 | 0.5 | 10 | 0.0998 | 73 | 8.2 |
| 1.2133 | 2.05 | 0.28 | −45 | 0.1 | 6 | 0.1054 | 97 | 8.7 |
| 1.2126 | 2.25 | 0.44 | −45 | 1 | 14 | 0.1008 | 88 | 8.8 |
| 1.2121 | 2.05 | 0.44 | −15 | 0.1 | 6 | 0.1001 | 60 | |
| 1.2131 | 2.15 | 0.36 | −30 | 0.5 | 10 | 0.1105 | 71 | 9.6 |
| 1.2127 | 2.05 | 0.44 | −45 | 0.1 | 14 | 0.1033 | 90 | 7.7 |
| 1.2135 | 2.24 | 0.44 | −16 | 0.1 | 14 | 0.1058 | 60 | |
| 1.2156 | 2.25 | 0.28 | −15 | 0.1 | 6 | 0.0983 | 65 | |
| 1.2131 | 2.05 | 0.44 | −14 | 1 | 14 | 0.1136 | <12 | |
| 1.2125 | 2.05 | 0.28 | −15 | 0.1 | 14 | 0.1022 | <11 | |
| 1.2118 | 2.15 | 0.36 | −30 | 0.5 | 10 | 0.1065 | 76 | 8.7 |
| 1.2116 | 2.15 | 0.36 | −30 | 0.5 | 10 | 0.0978 | 75 | 9.1 |
| 1.21 | 2.05 | 0.44 | −45 | 1 | 6 | 0.1009 | 94 | 8.7–8.9 |
| 1.2128 | 2.05 | 0.28 | 15 | 1 | 6 | 0.1114 | | |
| 1.2114 | 2.25 | 0.28 | −43 | 1 | 14 | 0.0999 | 67 | 9.5 |

DTPA=Diethylene triamine pentaacetic acid, measurement in grams.
TEA=Triethyl amine, measurement in milliliters.
IBCF=Isobutylchloroformate, measurement in milliliters.
Temp (IPCF)=temperature that the IBCF addition to DTPA was run under in degree Celsius.
[Bicarb]=Sodium bicarbonate concentration in Molar.
Bicarb volume=volume of sodium bicarbonate solution used to dissolve polylysine.
PL=mass of polylysine in grams.
Conj. %=% of lysine amino groups conjugated with pendant DTPA groups.
R1=relaxivity measure of the resulting isolated polymer.
Typical results for the method described by Sieving et al. (*Bioconjugate Chem*. 1:65–71, 1990) and three repetitions of the modified method, scaled up to 500mg initial polylsine-HBr are described in Table 2. It is seen that the desired surrogate marker for conformation is best for the modified reaction and that the previous method does not yield extended polymers after labeling with Gd in 4 synthesis runs.

TABLE 2

Degree of conjugation of DTPA and the relaxivity of polymeric products according to Method I and Method II

| Method | Conjugation, % | Relaxivity, R1 |
|---|---|---|
| Method I (Sieving) | 82 | 10 |
|  | 84 | 10.4 |
|  | 89 | 9.7 |
|  | 76 | 9.8 |
| Method II (Improved) | 93 | 8 |
|  | 94 | 7.4 |
|  | 90 | 7.7 |

The method II protocol is as follows:

500 mg of poly-L-lysine hydrobromide are dissolved in 60 mL of 0.1 M aqueous sodium bicarbonate solution having a pH of 9, which is then cooled in an ice bath to 0C. Then 6.05 g diethylaminetriaminepentaacetic acid, and 10.25 mL of triethylamine are added under nitrogen to 120 mL of dry, nitrogen purged acetonitrile. The solution is stirred at 50°–55° C. until the DTPA is dissolved, which typically requires ½ hour or longer. Under a dry nitrogen purge, the DTPA solution is cooled to −45° C., and 2.2 mL of isobutylchloroformate are added dropwise to the solution using a syringe. The solution becomes cloudy, turning to a grayish white slurry. After stirring for 1 hour, the resulting slurry is added dropwise to the polylysine/sodium bicarbonate solution under vigorous mixing at 0° C. The resulting mixture is allowed to warm slowly to room temperature and stirred for 15 to 20 additional hours. Standard biological separation techniques yield the purified, DTPA substituted polymer, which can then be derivatized further with appropriate cationic species.

From the foregoing, it is apparent that an extended linear polymer of Gd-DTPA-polylysine is an excellent MRI contrast agent for enhancing tumor contrast. In particular, it may delineate tumor angiogenesis parameters at a higher sensitivity than can be done with other MRI contrast agents. Such polymers could be used to deliver therapeautic agents as well, and labeling the polymer with positron emitting elements for use in positron emission tomography (PET) imaging would also be feasible. The key feature of the agent is its ability to penetrate the tumor endothelium and to be retained in the tumor intersitium for an extended period after injection into the blood stream.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A contrast agent for use in acquiring MRI images for the purpose of assessing tumor angiogenesis, said contrast agent comprising a linear extended poly(amino acid) copolymer to which a plurality of chelating groups comprising gadolinium is attached, said copolymer having a persistence length in a range from about 100 angstroms to about 600 angstroms, said contrast agent being administered into a subject to enhance a contrast in said MRI images of an internal region of said subject "wherein said copolymer is a random copolymer of glutamic acid and lysine".

2. The contrast agent of claim 1 wherein a chain length of the copolymer comprises from about 150 to about 500 residues.

3. The contrast agent of claim 1 wherein a chain length of the copolymer comprises from about 150 to about 250 residues.

4. The contrast agent of claim 1 wherein a chain length of the copolymer comprises from about 140 to about 150 residues.

5. The contrast agent according to claim 1, wherein said linear extended poly(amino acid) copolymer has a diameter in a range from about 20 to about 50 angstroms.

6. The contrast agent according to claim 1 wherein said chelating groups comprise diethylene triamine pentaacetic acid, which is conjugated to at least 90 percent of amino acid residues in a backbone of said copolymer.

7. The contrast agent according to claim 1, wherein a chain length of the copolymer comprises from about 150 to about 500 residues.

8. The contrast agent according to claim 1, wherein a chain length of the copolymer comprises from about 150 to about 250 residues.

9. The contrast agent according to claim 1, wherein said linear extended poly(amino acid) copolymer has a diameter in a range from about 20–50 angstroms.

* * * * *